United States Patent [19]

Rajagopalan

[11] 4,219,550

[45] Aug. 26, 1980

[54] CIS- AND TRANS-OCTAHYDROPYRIDOPYRROLOBENZ-HETEROCYCLES

[75] Inventor: Parthasarathi Rajagopalan, Graden City, N.Y.

[73] Assignee: E. I. Du Pont de Nemours and Company, Wilmington, Del.

[21] Appl. No.: 959,064

[22] Filed: Nov. 9, 1978

[51] Int. Cl.² .................. A61K 31/535; A61K 31/54; C07D 498/12; C07D 513/12
[52] U.S. Cl. ............................. 424/246; 260/244.4; 424/248.4; 424/248.57; 424/256; 544/14; 544/99; 544/101
[58] Field of Search ............... 544/14, 99; 546/66; 424/246, 248.4, 256; 260/244.4

[56] References Cited

U.S. PATENT DOCUMENTS

| | | |
|---|---|---|
| 3,914,421 | 10/1975 | Rajagopalan ...................... 544/99 X |
| 4,013,652 | 3/1977 | Rajagopalan .......................... 544/99 |
| 4,115,577 | 9/1978 | Rajagopalan ...................... 544/14 X |

*Primary Examiner*—Dolph H. Torrence

[57] ABSTRACT cis- and trans- Octahydropyridopyrrolobenzheterocycles of the formula:

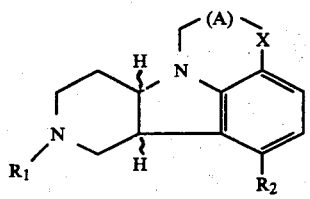

where $$A = -CH_2-, -\underset{\underset{CH_3}{|}}{CH}- \text{ or } -CH_2CH_2-;$$

X=O or S; $R_1$=H, $C_1$-$C_4$ straight or branched chain alkyl or cyclopropyl; and $R_2$=H, $CH_3$, $OCH_3$, Cl, Br, F or $CF_3$.

The compounds are useful as tranquilizers and antidepressants.

42 Claims, No Drawings

CIS- AND TRANS-OCTAHYDROPYRIDOPYRROLOBENZHETEROCYCLES

BACKGROUND OF THE INVENTION

Mental illnesses includes psychoses and neuroses. The symptoms requiring treatment include depression, anxiety, agitation and hallucinations. Drugs used particularly for treatment of both reactive and endogenous depressions include monoamine oxidase (MAO) inhibitors such as iproniazide, tranylcypromine, nialamide, phenelzine and paragyline and the non-MAO inhibiting tricyclic aromatic dibenzazepines such as imipramine and dibenzocycloheptadienes such as amitriptyline.

All of these drugs have side effects that limit their usefulness. The MAO inhibitors may cause tremors, insomnia, hyperhydrosis, agitation, hypermanic behavior, confusion, hallucinations, convulsions, orthostatic hypertension and death. They frequently cause dizziness, vertigo, headache, inhibition of ejaculation, difficulty in urination, weakness, fatigue, dry mouth, constipation and blurred vision. Imipramine may cause blurred vision, dryness of mouth, constipation, urinary retention, orthostatic hypotension, respiration depression, myocardial infarction and congestive heart failure. Similar difficulties are experienced with amitriptyline.

There is a genuine need for psychotherapeutic agents which are effective and have fewer side effects than the drugs in use today. The new and useful drugs disclosed here satisfy these criteria. They also have a beneficial tranquilizing action.

The compounds of this invention are cis- and trans-octahydropyridopyrrolobenzheterocycles. The compounds of the following patents can be reduced to form some of the novel compounds of this invention.

U.S. Pat. Nos. 3,914,421 and 4,013,652 disclose compounds of the formula:

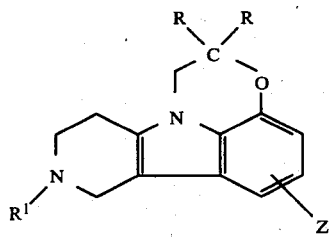

where
the R's are the same or different and are H or $CH_3$, and one of them can be $C_2$–$C_9$ alkyl or phenyl;
$R^1$ is hydrogen, $C_1$–$C_4$ alkyl, $C_3$–$C_6$ cycloalkyl, $C_2$–$C_4$ alkoxy-carbonyl, or substituted $C_1$–$C_4$ alkyl where the substituent is the $C_3$–$C_6$ cycloalkyl or phenyl; and Z is H, Cl or $CH_3$;
or its pharmaceutically suitable salts.

U.S. Pat. No. 4,115,577 discloses compounds of the formula:

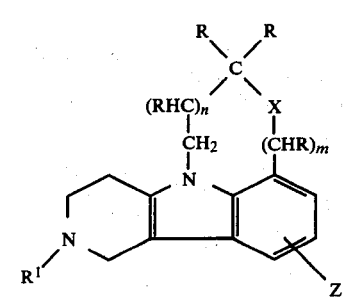

where
X is S, S or $SO_2$;
m and n are either 0 or 1 and the sum of m and n is at least 1;
the R's are the same or different and are H or $CH_3$, and one of them can be $C_2$–$C_9$ alkyl, phenyl, $C_7$–$C_{10}$ phenylalkyl, furyl, thienyl, pyridyl, phenyl or $C_7$–$C_{10}$ phenylalkyl substituted on adjacent ring carbon atoms with methylenedioxy, or phenyl or $C_7$–$C_{10}$ phenylalkyl substituted on the ring with 1, 2 or 3 substituents individually selected from methoxy, ethoxy, bromine, chlorine, fluorine, trifluoromethyl and $C_1$–$C_4$ alkyl; when X is S and m is 0, one R on the group —RCR— can be —$OCH_3$; and when X is S and m is 1, the R on the group $(CHR)_m$ can be —$OCH_3$;
$R^1$ is hydrogen, $C_{1-C4}$ alkyl, $C_3$–$C_5$ alkenyl, $C_3$–$C_5$ alkynyl, $C_3$–$C_6$ cycloalkyl, $C_2$–$C_4$ alkoxycarbonyl, trifluoroacetyl or substituted $C_1$–$C_4$ alkyl where the substituent is $C_3$–$C_6$ cycloalkyl, phenyl, phenyl substituted on adjacent carbon atoms with methylenedioxy, or phenyl substituted with 1, 2 or 3 substituents individually selected from methoxy, ethoxy, bromine, chlorine, fluorine, trifluoromethyl and $C_1$–$C_4$ alkyl; and
Z is H, Cl or $CH_3$;
and their pharmaceutically suitable salts.

Copending U.S. patent application Ser. No. 916,846 filed June 16, 1978 by P. Rajagopalan (which is a continuation-in-part of U.S. patent application Ser. No. 263,766 filed June 9, 1972 now abandoned) discloses a compound of the formula:

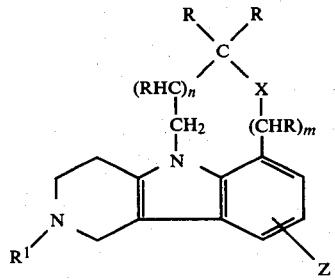

where
X is O, S,

or $SO_2$;

n is 0 or 1;
m is 0 or 1;
except that when X is O, the sum of n plus m is one or two; and when X is S,

or $SO_2$, n and m are both zero;

the R's are the same or different and are H or $CH_3$, and one of them can be $C_2$–$C_9$ alkyl, phenyl, $C_7$–$C_{10}$ phenylalkyl, furyl, thienyl, pyridyl, phenyl or $C_7$–$C_{10}$ phenylalkyl substituted on adjacent ring carbon atoms with methylenedioxy, or phenyl or $C_7$–$C_{10}$ phenylalkyl substituted on the ring with 1, 2 or 3 substituents individually selected from methoxy, ethoxy, bromine, chlorine, fluorine, trifluoromethyl and $C_1$–$C_4$ alkyl; when X is S one R on the group —RCR— can be —$OCH_3$;

$R^1$ is hydrogen, $C_1$–$C_4$ alkyl, $C_3$–$C_5$ alkenyl, $C_3$–$C_5$ alkynyl, $C_3$–$C_6$ cycloalkyl, $C_2$–$C_4$ alkoxycarbonyl, trifluoroacetyl or substituted $C_1$–$C_4$ alkyl where the substituent is $C_3$–$C_6$ cycloalkyl, phenyl, phenyl substituted on adjacent carbon atoms with methylenedioxy, or phenyl substituted with 1, 2 or 3 substituents individually selected from methoxy, ethoxy, bromine, chlorine, fluorine, trifluoromethyl and $C_1$–$C_4$ alkyl; and Z is H, Cl or $CH_3$;
and their pharmaceutically suitable salts.

SUMMARY OF THE INVENTION

This invention is a class of novel cis- and trans-octahydropyridopyrrolobenzheterocycles of the formula:

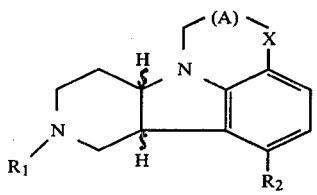

having a cis- or trans- configuration and where:

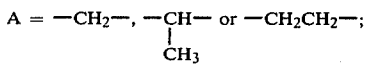

X=O or S;
$R_1$=H, $C_1$–$C_4$ straight or branched chain alkyl or cyclopropyl; and
$R_2$=H, $CH_3$, $OCH_3$, Cl, Br, F or $CF_3$.

Preferred compounds are those where:
(1.) the configuration is cis;
(2.) the cis configuration and a six-membered ring wherein independently:
A=—$CH_2$—;
X=O;
$R_1$=H; or
$R_2$=H;
(3.) the cis configuration and a seven-membered ring wherein independently:
A=—$CH_2CH_2$—;
X=S;
$R_1$=H; or
$R_2$=H;
(4.) the trans configuration wherein independently:
A=—$CH_2$—; or
X=S.

Most preferred compounds are those as follows:
(a.) a compound of the cis configuration wherein:
A=—$CH_2$—;
X=O;
$R_1$=H; and
$R_2$=H;
(b.) a compound of the cis configuration wherein:
A=—$CH_2CH_2$—;
X=S;
$R_1$=H; and
$R_2$=H;
(c.) the trans configuration wherein:
A=—$CH_2$—;
X=S;
$R_1$=—$CH_2$—$CH_3$; and
$R_2$=H.

The compounds are useful as tranquilizers and antidepressants.

The invention also includes pharmaceutical preparations containing the compounds, their pharmaceutically suitable salts and methods for tranquilizing and combatting depression in warm-blooded animals by administration thereof.

DETAILED DESCRIPTION OF THE INVENTION

In more detail, the novel cis- and trans- octahydropyridopyrrolobenzheterocycles of formula I are prepared as follows:

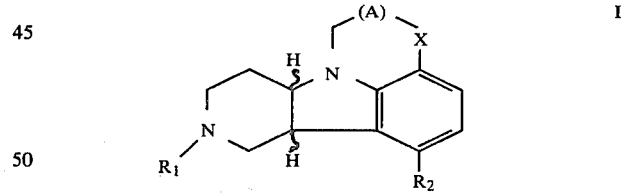

Compounds of the type where the hydrogens in the 6b- and 10a- positions are cis with respect to each other can be prepared by reduction of the compounds of formula II or their salts (which have been described in U.S. Pat. Nos. 3,914,421 and 4,013,652) with hydrogen in the presence of a catalyst such as platinum or palladium on carbon, or with a metal such as zinc and a mineral acid such as hydrochloric acid, or with sodium in liquid ammonia, or with a borane-amine complex such as borane-triethylamine in tetrahydrofuran, or preferably with sodium cyanoborohydride in acetic or trifluoroacetic acid. The reaction can conveniently be carried out at temperatures of −30° to +120° centigrade.

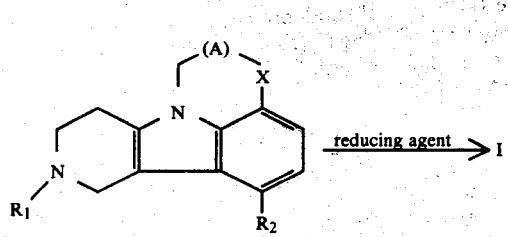

Compounds of the type where the hydrogens in the 6b- and 10a- positions are trans with respect to each other can be prepared by reacting compounds of the formula II where $R_1$ is other than H or COOR groups (which have been described in U.S. Pat. Nos. 3,914,421 and 4,013,652) with $BH_3 \cdot THF$ in the tetrahydrofuran or the hydrochloride salts of II with sodium borohydride in diethylene glycol dimethyl ether followed by treatment with a strong mineral acid such as hydrochloric acid. The reactions can conveniently be run at temperatures of 25° to 150° centigrade depending upon the solvents. In the following examples, illustrative of the invention, all temperatures are in degrees centigrade, unless otherwise noted.

EXAMPLE 1

(+)-cis-1,2,6b,7,8,9,10,10a-Octahydropyrido[3', 4': 4,5]pyrrolo[1,2,3-de][1,4]benzoxazine Powdered sodium cyanoborohydride (25 g) is added, in small portions, to a well-stirred and cooled (5°) solution of 1,2,7,8,9,10-hexahydropyrido[3', 4': 4,5]pyrrolo[1,2,3-de][1,4]benzoxazine (20 g) in trifluoroacetic acid (250 ml) at such a rate that excessive frothing is avoided. After the addition is complete, the mixture is stirred at room temperature for 2 hours, treated with 6N hydrochloric acid (150 ml), and refluxed for 30 minutes. It is then cooled and basified with 25% sodium hydroxide and extracted thrice with chloroform. The combined chloroform extracts are washed thoroughly with water, dried over magnesium sulfate, and stripped of the solvent under reduced pressure to furnish a crystalline solid which is recrystallized from hexane to yield the title compound, m.p. 112°–113°.

The compounds listed below can be prepared by a similar procedure.

cis-1,2,6b,7,8,9,10,10a-Octahydropyrido-[3',4':4,5]pyrrolo[1,2,3-de][1,4]benzoxazines

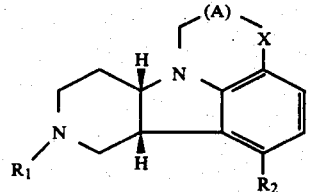

| Ex. | $R_1$ | $R_2$ | A | X | Salt | M.P. |
|---|---|---|---|---|---|---|
| 1 | H | H | $CH_2$ | O | | 112°–113° |
| 2 | H | Cl | $CH_2$ | O | | 83°–85° |
| 3 | cyclopropyl | H | $CH_2$ | O | | 121°–122° |
| 4 | H | H | $(CH_2)_2$ | O | | 100°–101° |
| 5 | H | H | $CH_2$ | S | | 123°–124° |
| 6 | $CH_3$ | H | $CH_2$ | S | | 116°–117° |
| 7 | cyclopropyl | H | $CH_2$ | S | hydrochloride | 229°–230° (dec) |
| 8 | H | H | $(CH_2)_2$ | S | hydrochloride | 72°–73° |
| 9 | cyclo- | H | $(CH_2)_2$ | | | 265°–266° | cis-1,2,6b,7,8,9,10,10a-Octahydropyrido-[3',4':4,5]pyrrolo[1,2,3-de][1,4]benzoxazines

| Ex. | $R_1$ | $R_2$ | A | X | Salt | M.P. |
|---|---|---|---|---|---|---|
| 10 | propyl H | H | $CH_3$ $\mid$ $-CH-$ | S | hydrochloride | (dec) 239°–241° (dec) |
| 11 | $(CH_3)_2CH$ | H | $CH_2$ | S | hydrochloride | 229°–231° (dec) |
| 12 | $CH_3CH_2-$ | H | $CH_2$ | S | 2-naphthalene sulfonate | 121°–123° |
| 13 | $CH_3CH_2CH_2$ | H | $CH_2$ | O | | |
| 14 | H | $OCH_3$ | $CH_2$ | O | | |
| 15 | H | $CH_3$ | $CH_2$ | O | | |

EXAMPLE 16

(+)-trans-8-Ethyl-1,2,6b, 7,8,9,10,10a-octahydropyrido[3',4':4,5]pyrrolo[1,2,3-de][1,4]benzothiazine A 1 M solution of borane in tetrahydrofuran (80 ml) is added slowly to a stirred solution-suspension of 8-acetyl-1,2,7,8,9,10-tetrahydropyrido[3', 4':- 4,5]pyrrolo[1,2,3-de][1,4]benzothiazine (5.5 g) in anhydrous tetrahydrofuran (100 ml) and, after the addition is complete, the mixture is stirred and refluxed for 90 minutes and cooled to room temperature. Excess of borane is then decomposed by the dropwise addition of 6N hydrochloric acid after which the mixture is diluted with 6N hydrochloric acid (60 ml) and refluxed for 30 minutes. The mixture is evaporated to dryness under reduced pressure and the residual solid is treated with 50 ml of 10% sodium hydroxide and extracted with chloroform. The chloroform extract is washed with water, dried over magnesium sulfate and stripped of the solvent under reduced pressure to yield a viscous liquid which is dissolved in 100 ml of anhydrous ether and added to excess of anhydrous ether saturated with hydrogen chloride gas. The hydrochloride that separated is filtered off, washed thoroughly with anhydrous ether and recrystallized from methanol to yield the title compound as its hydrochloride, m.p. 315°–317° (dec).

The compounds listed below can be prepared by a similar procedure.

trans-1,2,6b,7,8,9,10,10a-Octahydropyrido[3',4':4,5]-pyrrolo[1,2,3-de][1,4]benzothiazines

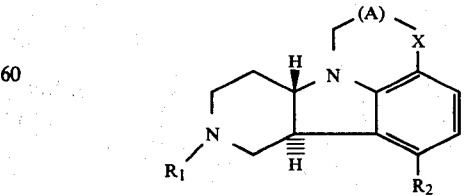

| Ex. | $R_1$ | $R_2$ | A | X | Salt | m.p. |
|---|---|---|---|---|---|---|
| 17 | cyclopropyl | H | $CH_2$ | O | | 82°–86° |
| 18 | $CH_3$ | H | $CH_2$ | S | hydrochloride | 215°–217° (dec) |

-continued trans-1,2,6b,7,8,9,10,10a-Octahydropyrido[3',4':4,5]-
pyrrolo[1,2,3-de][1,4]benzothiazines

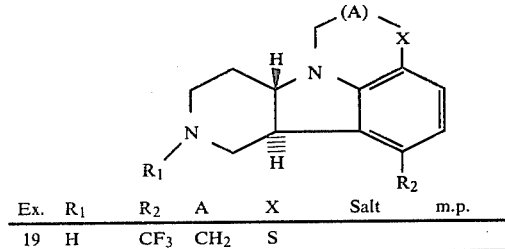

| Ex. | $R_1$ | $R_2$ | A | X | Salt | m.p. |
|---|---|---|---|---|---|---|
| 19 | H | $CF_3$ | $CH_2$ | S | | |

EXAMPLE 20

The starting material for the preparation of the compound in Example 16, i.e., 8-acetyl-1,2,7,8,9,10-hexahydropyrido[3', 4': 4,5]pyrrolo[1,2,3-de][1,4]-benzothiazine, is prepared according to the following procedure:

8-Acetyl-1,2,7,8,9,10-hexahydropyrido[3',4':4,5]-pyrrolo[1,2,3-de][1,4]benzothiazine Zinc dust (80 g) is added, in small portions, to a vigorously stirred mixture of 2,3-dihydro-4-nitroso-4H-1,4-benzothiazine (36 g) in glacial acetic acid (400 ml) such that the temperature is maintained below 30°. After the addition is complete the mixture is stirred at room temperature and filtered into a filter flask containing 1-acetyl-4-piperidone (28.2 g) in glacial acetic acid (50 ml). The filter cake is washed with a small quantity of acetic acid and the combined filtrate and washings are refluxed for 45 minutes and then stripped of the excess of acetic acid under reduced pressure. The residual viscous liquid is taken up in ethanol, cooled, and scratched. The solid that separates is filtered off, washed with a small quantity of ethanol and then with water and recrystallized from methanol to yield the title compound, m.p. 161°–163° C.

Utility

The compounds of this invention can be administered as treatment for psychiatric depressions of the reactive and endogenous types according to the invention by any means that effects contact of the active ingredient compound with the site of action in the body of a warm-blooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipient, the type and severity of depression, kind of concurrent treatment, if any, frequency of treatment and the nature of the effect desired.

The compounds of this invention can be administered orally at doses of about 0.01–100 mg/kg or preferably at 0.05–25 mg/kg or more preferably at 0.10–10 mg/kg. The useful daily human oral dose for the more potent compounds of the invention is expected to be in the range of 20–500 mg. A typical dosage form could be a capsule or a compressed tablet containing 10, 25 or 50 mg active ingredient administered 1–4 times daily.

The antidepressant activity of the compounds is evidenced by tests conducted in female white mice in which prevention of tetrabenazine-induced sedation and depression is demonstrated. This mouse test is predictive of human antidepressant response (Everett, "The Dopa Response Potentiation Test and Its Use in Screening for Antidepressant Drugs", pp 164 in "Antidepressant Drugs" [Proceedings of the First International Symposium], S. Garattini and M. N. G. Dukes, eds., 1967).

EXAMPLE A

Groups of 10 Carworth $CF_1S$ female mice, 18–21 g each, were fasted 1.5 hours and were intubated with antagonist compounds at oral doses of 0, 0.33, 1, 3, 9, 27 and 81 mg/kg in 0.20 ml of 1% Methocel ®. The mice were challenged 30 minutes later with tetrabenazine (as the methane-sulfonate), 32 mg/kg intraperitoneally (dissolved in 0.20 ml 0.05 M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5"×8" with 0.33" mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes. Table 1 gives results.

The tranquilizing activity of the compounds of this invention is evidenced by tests conducted in male white rats in which a conditioned avoidance response is interrupted following an oral dose of the drug. This test is predictive of human response to an antipsychotic (tranquilizing) drug. The method of Clark was used (Clark, R., Psychon. Sci. 6, 11, 1966).

EXAMPLE B

The test animals, male Holtzman rats between 90 and 115 grams, were food deprived 18 hours prior to avoidance training. Test drugs were suspended in 0.5% Methocel.

The equipment consisted of a plexiglas pit 5"×5"×9" fitted with a metal floor grid which can be electrified via the output of a shock generator. The top end of the pit opened into a surrounding platform 12"×3-½" on all four sides. This pit fitted into a larger plexiglas housing which served both to support the pit and to distribute wires to (a) the electrified floor grid, (b) a sound speaker used for stimulus presentation and (c) a 40 watt incandescent bulb also used for stimulus presentation. The main housing was separate from but attached to a metal frame which supported a noise generator, shock generator, and timing/sequence device. The noise generator was a Grason-Stadler Model 1724, used in the 50 KHz bandwidth with output of −10DB. The two-line shock generator supplied a constant A/C current of 0.19 milliamperes, via constantly scrambled 10 HZ square wave output.

The rats were trained by giving each of them four successive trials 15 to 20 minutes apart with a conditioned stimulus (CS) of a 40-watt incandescent bulb and a white noise plus an unconditioned stimulus (US) of a 0.19 milliampere scrambled shock. Following the four CS+US trials each animal was given an avoidance learning criterion trial in which the CS was presented alone 10 seconds prior to the US.

Rats were dosed orally with compound of the invention or standard drug, 20 rats/dose. Each rat was tested at 60, 120 and 240 minutes after drug.

Comparative data are in Table 1.

TABLE 1

MOUSE TETRABENAZINE (TBZ) ANTAGONISM AND
RAT CONDITIONED AVOIDANCE RESPONSE (CAR)
ED50 VALUES FOR TEST COMPOUNDS OF THE INVENTION
AND THE STANDARD ANTIDEPRESSANT AMITRIPTYLINE

| EX. | A | X | $R_1$ | $R_2$ | CONFIG-URATION | TBZ ANTAG. PTOSIS | TBZ ANTAG. EXPLOR. | CAR AVOID. | CAR ESCAPE |
|---|---|---|---|---|---|---|---|---|---|
| 1. | $CH_2$ | O | H | H | cis | 1.4 | 23. | -2.2 | >25. |
| 2. | $CH_2$ | O | H | Cl | cis | 4.3 | 27. | ~23. | >50. |
| 3. | $CH_2$ | O | ◁ | H | cis | 21. | 24. | 28. | |
| 4. | $CH_2CH_2$ | O | H | H | cis | 1.6 | 47. | 2.2 | 14. |
| 5. | $CH_2$ | S | H | H | cis | 3.3 | .4 | 1.1 | |
| 6. | $CH_2$ | S | $CH_3$ | H | cis | 7.2 | >81. | 17. | |
| 7. | $CH_2$ | S | ◁ | H | cis | 1.1 | 3.3 | | |
| 8. | $CH_2CH_2$ | S | H | H | cis | * | | | |
| 8a. | $CH_2CH_2$ | S | H | H | cis | 6.6 | 54. | 2.2 | |
| 9. | $CH_2CH_2$ | S | ◁ | H | cis | 68. | 68. | | |
| 10. | CH CH$_3$ | S | H | H | cis | 23. | 27. | 8.5 | ~38. |
| 11. | $CH_2$ | S | $(CH_3)_2$—CH | H | cis | 11. | 14. | 5.5 | |
| 16. | $CH_2$ | S | $C_2H_5$ | H | trans | 7.5 | 10.8 | 6.2 | |
| 17. | $CH_2$ | O | ◁ | H | trans | 7.5 | 11.2 | | |
| 18. | $CH_2$ | S | $CH_3$ | H | trans | 6.5 | 6.5 | 28. | |
| | $CH_2$ | S | n-$C_4H_9$ | H | cis | 11. | 14. | 5.5 | |
| | Amitriptyline · HCl | | | | | 1.6 | 4.3 | 116. | |
| | Chlorpromazine · HCl | | | | | >81. | >81. | 5.4 | ~34. |

*HCl salt of No. 8a; active subcutaneously at 30 mg/kg

The compounds can be formulated into compositions comprising a compound of formula I or a pharmaceutically suitable acid-addition salt thereof together with a pharmaceutically suitable carrier. The carrier can be either a solid or liquid and the compositions can be in the form of tablets, liquid-filled capsules, dry-filled capsules, aqueous solutions, non-aqueous solutions, suppositories, syrups, suspensions and the like. The compositions can contain suitable preservatives and coloring and flavoring agents. Some examples of the carriers which can be used in the preparation of the products of this invention are gelatin capsules; sugars, such as lactose and sucrose; starches; dextrans; cellulosics, such as methyl cellulose, cellulose acetate phthalate; gelatin, talc; steric acid salts; vegetable oils, such as peanut oil, cottonseed oil, sesame oil, olive oil, corn oil, and oil of theobroma; liquid petrolateum; polyethylene glycol; glycerin, sorbitol; propylene glycol; ethanol; agar; water; and isotonic saline.

In formulating the compounds, conventional practices and precautions are used. The composition intended for parenteral administration must be sterile either by using sterile ingredients and carrying out the production under aseptic conditions or by sterilizing the final composition by one of the usual procedures such as autoclaving under appropriate temperature and pressure conditions. Customary care should be exercised so that no incompatible conditions exist between the active components and the diluent preservative or flavoring agent, or in the conditions employed in preparation of the compositions.

What is claimed is:

1. A compound of the formula:

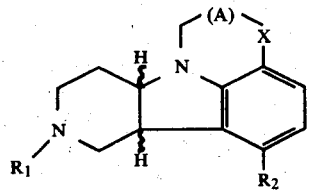

having a cis or trans configuration and where:

$$A = -CH_2-, -CH-, \text{ or } -CH_2CH_2-;$$
$$\phantom{A = -CH_2-, -}CH_3$$

X=O or S;
$R_1$=H, $C_1$-$C_4$ straight or branched chain alkyl or cyclopropyl; and
$R_2$=H, $CH_3$, $OCH_3$, Cl, Br, F or $CF_3$;
or pharmaceutically suitable salts thereof.

2. A compound of claim 1 where the configuration is cis.

3. A compound of claim 1 where the configuration is cis and A is —$CH_2$—.

4. A compound of claim 1 where the configuration is cis, A is —$CH_2$— and X is O.

5. A compound of claim 1 where the configuration is cis, A is —$CH_2$— and $R_1$ is H.

6. A compound of claim 1 where the configuration is cis, A is —$CH_2$— and $R_2$ is H.

7. A compound of claim 1 where the configuration is cis and A is —$CH_2CH_2$—.

8. A compound of claim 1 where the configuration is cis, A is —$CH_2CH_2$— and X is S.

9. A compound of claim 1 where the configuration is cis, A is —CH$_2$CH$_2$— and R$_1$ is H.

10. A compound of claim 1 where the configuration is cis, A is —CH$_2$CH$_2$— and R$_2$ is H.

11. A compound of claim 1 where the configuration is trans, A is —CH$_2$— and X is S.

12. The compound of claim 1 where the configuration is trans and A is —CH$_2$—, X is S, R$_1$ is —CH$_2$CH$_3$ and R$_2$ is H.

13. The compound of claim 1 where the configuration is cis, A is —CH$_2$—, X is O, R$_1$ is H and R$_2$ is H.

14. The compound of claim 1 where the configuration is cis, A is —CH$_2$CH$_2$—, X is S, R$_1$ is H and R$_2$ is H.

15. A pharmaceutical composition suitable for use in warm-blooded animals consisting essentially of a pharmaceutically suitable vehicle and an effective antidepressant amount of a compound of the formula:

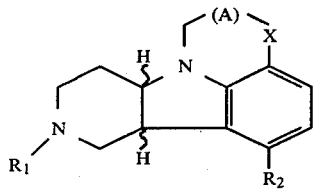

having a cis or trans configuration and where:

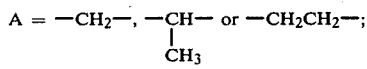

X = O or S;
R$_1$ = H, C$_1$-C$_4$ straight or branched chain alkyl or cyclopropyl; and
R$_2$ = H, CH$_3$, OCH$_3$, Cl, Br, F or CF$_3$; or pharmaceutically suitable acid salts thereof.

16. The pharmaceutical composition of claim 15 where the configuration is cis.

17. The pharmaceutical composition of claim 15 where the configuration is cis and A is —CH$_2$—.

18. The pharmaceutical composition of claim 15 where the configuration is cis, A is —CH$_2$— and X is O.

19. The pharmaceutical composition of claim 15 where the configuration is cis, A is —CH$_2$— and R$_1$ is H.

20. The pharmaceutical composition of claim 15 where the configuration is cis, A is —CH$_2$— and R$_2$ is H.

21. The pharmaceutical composition of claim 15 where the configuration is cis and A is —CH$_2$CH$_2$—.

22. The pharmaceutical composition of claim 15 where the configuration is cis, A is —CH$_2$CH$_2$— and X is S.

23. The pharmaceutical composition of claim 15 where the configuration is cis, A is —CH$_2$CH$_2$— and R$_1$ is H.

24. The pharmaceutical composition of claim 15 where the configuration is cis, A is —CH$_2$CH$_2$— and R$_2$ is H.

25. The pharmaceutical composition of claim 15 where the configuration is trans, A is —CH$_2$— and X is S.

26. The pharmaceutical composition of claim 15 where the configuration is trans, A is —CH$_2$—, X is S, R$_1$ is —CH$_2$CH$_3$ and R$_2$ is H.

27. The pharmaceutical composition of claim 15 where the configuration is cis, A is —CH$_2$—, X is O, R$_1$ is H and R$_2$ is H.

28. The pharmaceutical composition of claim 15 where the configuration is cis, A is —CH$_2$CH$_2$—, X is S, R$_1$ is H and R$_2$ is H.

29. A method of combatting depression in a warm-blooded animal which comprises administering to the animal an effective antidepressant amount of a compound of formula

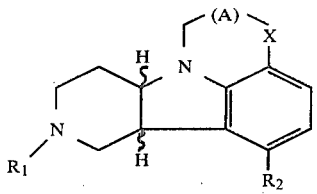

having a cis or trans configuration and where:

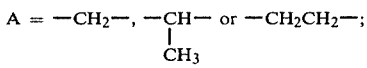

X = O or S;
R$_1$ = H, C$_1$-C$_4$ straight or branched chain alkyl or cyclopropyl; and
R$_2$ = H, CH$_3$, OCH$_3$, Cl, Br, F or CF$_3$; or pharmaceutically suitable acid salts thereof.

30. The method of combatting depression of claim 29 where the configuration is cis.

31. The method of combatting depression of claim 29 where the configuration is cis and A is —CH$_2$—.

32. The method of combatting depression of claim 29 where the configuration is cis, A is —CH$_2$— and X is O.

33. The method of combatting depression of claim 29 where the configuration is cis, A is —CH$_2$— and R$_1$ is H.

34. The method of combatting depression of claim 29 where the configuration is cis, A is —CH$_2$— and R$_2$ is H.

35. The method of combatting depression of claim 29 where the configuration is cis and A is —CH$_2$CH$_2$—.

36. The method of combatting depression of claim 29 where the configuration is cis, A is —CH$_2$CH$_2$— and X is S.

37. The method of combatting depression of claim 29 where the configuration is cis, A is —CH$_2$CH$_2$— and R$_1$ is H.

38. The method of combatting depression of claim 29 where the configuration is cis, A is —CH$_2$CH$_2$— and R$_2$ is H.

39. The method of combatting depression of claim 29 where the configuration is trans, A is —CH$_2$— and X is S.

40. The method of combatting depression of claim 29 where the configuration is trans and A is —CH$_2$—, X is S, R$_1$ is —CH$_2$CH$_3$ and R$_2$ is H.

41. The method of combatting depression of claim 29 where the configuration is cis, A is —CH$_2$—, X is O, R$_1$ is H and R$_2$ is H.

42. The method of combatting depression of claim 29 where the configuration is cis, A is —CH$_2$CH$_2$—, X is S, R$_1$ is H and R$_2$ is H.

* * * * *